United States Patent
Li et al.

(10) Patent No.: US 12,409,143 B2
(45) Date of Patent: Sep. 9, 2025

(54) SOFTGEL CAPSULES AND A METHOD FOR PREPARING THE SOFTGEL CAPSULES

(71) Applicant: R.P. Scherer Technologies, LLC, Carson City, NV (US)

(72) Inventors: Haitao Li, St. Petersburg, FL (US); Qi Fang, St. Petersburg, FL (US); Karunakar Sukuru, St. Petersburg, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

(21) Appl. No.: 18/842,531

(22) PCT Filed: Dec. 13, 2023

(86) PCT No.: PCT/US2023/083754
§ 371 (c)(1),
(2) Date: Aug. 29, 2024

(87) PCT Pub. No.: WO2024/129811
PCT Pub. Date: Jun. 20, 2024

(65) Prior Publication Data
US 2025/0108012 A1    Apr. 3, 2025

Related U.S. Application Data

(60) Provisional application No. 63/432,445, filed on Dec. 14, 2022.

(51) Int. Cl.
*A61K 9/48* (2006.01)
*A61K 47/02* (2006.01)

(52) U.S. Cl.
CPC .......... *A61K 9/4816* (2013.01); *A61K 9/4833* (2013.01); *A61K 47/02* (2013.01)

(58) Field of Classification Search
CPC .... A61K 9/4816; A61K 9/4833; A61K 47/02; A61K 33/06; A61J 3/07
See application file for complete search history.

(56) References Cited

U.S. PATENT DOCUMENTS

| | | |
|---|---|---|
| 2004/0013721 A1 | 1/2004 | Antipov et al. |
| 2010/0055174 A1 | 3/2010 | Xie et al. |
| 2017/0348249 A1 | 12/2017 | Suñé Negre et al. |

FOREIGN PATENT DOCUMENTS

| | | |
|---|---|---|
| CN | 212856926 U | 4/2021 |
| WO | 2022/104338 A1 | 5/2022 |

OTHER PUBLICATIONS

International Search Report and Written Opinion of International Application No. PCT/US2023/083754 mailed Apr. 8, 2024, 11 pgs.

*Primary Examiner* — David Browe
(74) *Attorney, Agent, or Firm* — Lowenstein Sandler LLP

(57) ABSTRACT

Disclosed herein is a method for preparing a softgel capsule including treating a softgel capsule with a solution including calcium salt, wherein the softgel capsule includes a fill material and a shell composition including pectin.

19 Claims, 1 Drawing Sheet

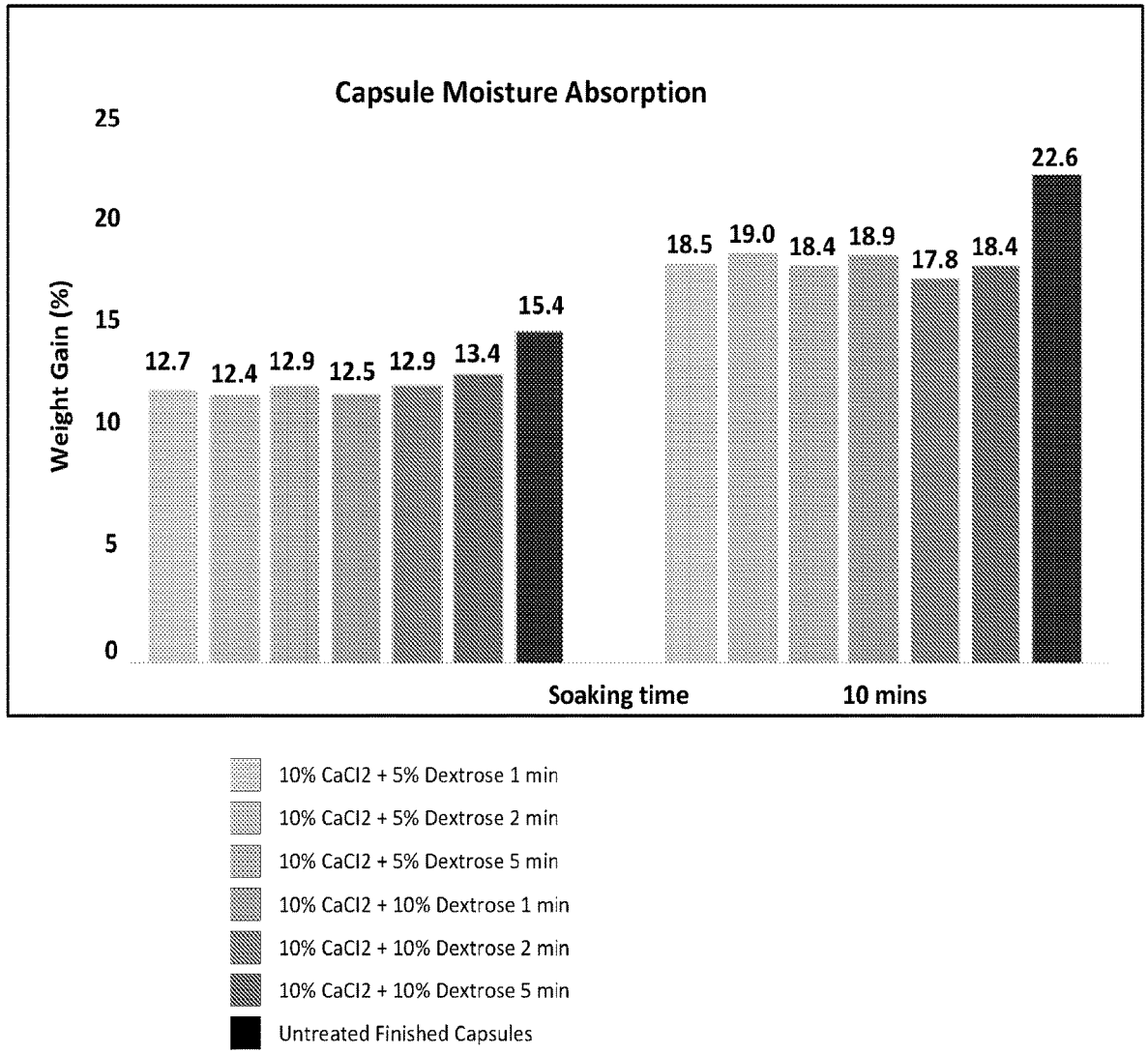

SOFTGEL CAPSULES AND A METHOD FOR PREPARING THE SOFTGEL CAPSULES

CROSS REFERENCE TO RELATED APPLICATION(S)

The present application claims priority to U.S. Provisional Patent Application No. 63/432,445 filed on Dec. 14, 2022, the entire contents of which are incorporated herein in its entirety.

FIELD OF THE INVENTION

The present invention relates to a method for preparing a softgel capsule including treating the softgel capsule with a solution including a calcium salt, such as calcium chloride. A softgel capsule is also provided including a fill material and a shell composition, wherein the shell composition includes calcium ions.

BACKGROUND OF THE INVENTION

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

Efforts have been made to create enteric dosage forms. Enteric dosage forms are designed to protect the contents of the dosage form from gastric conditions. For example, enteric dosage forms have been developed in which conventional enteric polymers (i.e., acid-insoluble polymers) are added in the capsule shell. It has been found that electrostatic attraction may occur in such capsules shell such that a complex coacervates may form in the shell, which are insoluble in acidic pH but dissolve at neutral and basic pH.

Accordingly, there is currently a need to improve the method of preparing the softgel capsule to improve the pH tolerance in enteric dissolution and disintegration and robustness of the shell.

SUMMARY OF THE INVENTION

The present invention is directed to a method for preparing a softgel capsule. The method includes treating a softgel capsule with a solution including a calcium salt, such as calcium chloride, wherein the softgel capsule comprises a fill material and a shell composition. In some embodiments, the solution may further include hydrochloric acid. In some embodiments, the solution may further include water. In some embodiments, the solution may further include a sugar. The sugar may be dextrose.

In some embodiments of the method, the calcium salt may be included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the solution.

In some embodiments, the solution may have a pH of less than about 3.

In some embodiments, the dextrose may be included in an amount of about 0.1 wt % to about 20 wt %, about 1 wt % to about 19 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the solution.

In some embodiments, the shell composition may include a plasticizer, pectin, gellan gum, dextrose, gelatin, or a combination thereof. In some embodiments of the shell composition, the plasticizer may include glycerin, sorbitol, sorbitol sorbitan solution, triacetin, polysorbate, or combinations thereof. In other embodiments, the plasticizer may include glycerin, sorbitol sorbitan solution, or a combination thereof. In yet another embodiment, the plasticizer may be sorbitol sorbitan solution.

In some embodiments, the method may further include drying the capsules after treating the capsules. In some embodiments, the drying may be performed by tumble drying the capsules. The drying may occur for about 1 hour, about 1.5 hours, about 2 hours, about 3 hours, or about 4 hours. In some embodiments, the drying may be performed in a drying chamber or a drying tunnel.

In some embodiments of the method, the treating may include using a washing/chilling treatment equipment for a pre-determined time period. The washing/chilling treatment equipment may be fully automatic. In some embodiments, the pre-determined time period is about 2.5 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 2 minutes, about 3 minutes, about 4 minutes, about 5 minutes, about 6 minutes, about 7 minutes, about 8 minutes, about 9 minutes, or about 10 minutes.

In another embodiment of the present disclosure, a softgel capsule is provided. The softgel capsule includes a fill material including an active agent and a shell composition, wherein the shell composition includes calcium ions.

In some embodiments, the shell composition may include pectin. The pectin may be low methoxy pectin. In some embodiments, the pectin may be included in an amount of about 1 wt % to about 25 wt %, about 2 wt % to about 20 wt %, 5 wt % to about 18 wt %, 7.5 wt % to about 15 wt %, or about 10 wt % to about 12 wt %, based on total weight of the shell composition.

In some embodiments, the shell composition may include a plasticizer. In some embodiments, the plasticizer may include glycerin, sorbitol, sorbitol sorbitan solution, triacetin, polysorbate, or combinations thereof. In another embodiment, the plasticizer may include glycerin and sorbitol sorbitan solution. In some embodiments, the polysorbate may include Tween 20, Tween 80, or combinations thereof.

In some embodiments, the plasticizer may be included in an amount of about 5 wt % to about 60 wt %, about 10 wt % to about 55 wt %, about 15 wt % to about 50 wt %, about 20 wt % to about 45 wt %, or about 25 wt % to about 35 wt % based on total weight of the shell composition.

In some embodiments, the shell composition may include gelatin. In some embodiments, the gelatin may be selected from the group consisting of Type A gelatin, Type B gelatin, and mixtures thereof. In some embodiments, the gelatin may be selected from the group consisting of fish gelatin, hide gelatin, bone gelatin and mixtures thereof. In some embodiments, the gelatin may be included in an amount of about 15 wt % to about 60 wt %, about 20 wt % to about 55 wt %, about 25 wt % to about 50 wt %, about 30 wt % to about 45 wt %, or about 35 wt % to about 40 wt % based on total weight of the shell composition.

In some embodiments, the shell composition may include gellan gum. The gellan gum may be included in an amount of about 0.001 wt % to about 5 wt %, about 0.01 wt % to about 4 wt %, about 0.1 wt % to about 3 wt %, or about 1 wt % to about 2 wt % based on total weight of the shell composition.

In some embodiments, the shell composition may include dextrose. The dextrose may be included in an amount of about 0.001 wt % to about 5 wt %, about 0.01 wt % to about 4.5 wt %, about 0.05 wt % to about 4 wt %, about 0.1 wt % to about 3 wt %, or about 1 wt % to about 2.5 wt % based on total weight of the shell composition.

In some embodiments, the softgel capsule may be treated with a treatment solution comprising a calcium salt. The calcium salt may be calcium chloride, calcium citrate, calcium gluconate, calcium lactate or any other soluble calcium salts. The calcium salt may be included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the treatment solution.

In some embodiments, the treatment solution may further include water. In some embodiments, the treatment solution may further include a sugar. The sugar may include dextrose. The dextrose may be included in an amount of about 0.1 wt % to about 20 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the treatment solution.

In some embodiments, the treatment solution may further include hydrochloric acid.

In some embodiments, the treatment may provide a weight gain of about 1% to about 10% of the capsule. In some embodiments, the capsule may have an improved burst strength when compared to a capsule without calcium treatment.

In some embodiments, the capsule does not rupture at a pH of 1.2 at 15 minutes, 30 minutes, 45 minutes, 60 minutes, 75 minutes, 90 minutes, 105 minutes, or 120 minutes when measured with a USP Apparatus II with paddles at 50 RPM, or 100 RPM in 0.1N hydrochloric (HCl) acid acidic media.

In some embodiments, the capsule does not rupture at a pH of 3.0, pH of 4.0, pH of 5.0 at 15 minutes, 30 minutes, 45 minutes, 60 minutes, 75 minutes, or 90 minutes when measured with a USP Apparatus II with paddles at 50 RPM, or 100 RPM in acidic media with above pH.

In some embodiments, the capsule ruptures at a pH of between 6 and 8 at 5 minutes, 10 minutes, 15 minutes, 20 minutes, 25 minutes, 30 minutes, 35 minutes, 40 minutes, 45 minutes, 50 minutes, 55 minutes, or 60 minutes when measured with a USP Apparatus II with paddles at 50 RPM, 100 RPM, 150 RPM, or 200 RPM in phosphate buffer.

BRIEF DESCRIPTION OF THE DRAWINGS

The present disclosure is illustrated by way of example, and not by way of limitation, in the figures of the accompanying drawings.

The FIGURE shows the capsule moisture absorption comparison between tested capsules according to an Example of the present disclosure.

DETAILED DESCRIPTION OF THE INVENTION

The present disclosure advances the state of the art by developing a treatment method for preparing softgel capsules. The method of the present disclosure initiates the ionotropic gelation rapidly and a certain degree of gelatin and pectin crosslinking by dextrose in order to enhance the enteric functionality and physical robustness of the capsule. By treating the softgel capsules with a solution including calcium, it was found to initiate the ionotropic gelation (calcium bridging effect). Thus, inventors believe that calcium ions bridge the shell composition to form a larger and stronger enhanced network.

As used herein, the term "enteric" is used to refer to the dissolution or disintegration resistant property of a substance such that dissolution or disintegration does not occur in a gastric environment. For example, the embodiments described herein include an enteric shell composition that dissolves in biological, artificial or simulated intestinal fluid rather than in biological, artificial or simulated gastric fluid. The embodiments described herein may include a coating having an enteric polymer.

As used herein, "pharmaceutically active ingredient" refers to a drug or compound that may be used in the diagnosis, cure, mitigation, treatment, or prevention of a condition. The term "condition" or "conditions" refers to those medical conditions that can be treated or prevented by administration to a subject of an effective amount of an active agent. Exemplary non-limiting conditions that may benefit from enteric softgel capsules may include, without limitations, capsules containing lactic acid bacteria, fish oil capsules, proton pump inhibitors, aspirin and similar products.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

Any pharmaceutically active ingredient may be used for purposes of the present invention, including both those that are water-soluble and those that are poorly soluble in water. Suitable pharmaceutically active ingredients include, without limitation, analgesics and anti-inflammatory agents, antacids, anthelmintic, anti-arrhythmic agents, anti-bacterial agents, anti-coagulants, anti-depressants, anti-diabetics, anti-diarrheal, anti-epileptics, anti-fungal agents, anti-gout agents, anti-hypertensive agents, anti-malarial, anti-migraine agents, anti-muscarinic agents, anti-neoplastic agents and immunosuppressants, anti-protozoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, stimulants, and combinations thereof.

In some embodiments, the active pharmaceutical ingredient may be selected, without limitations, from the group consisting of dabigatran, dronedarone, ticagrelor, iloperidone, ivacaftor, midostaurine, asimadoline, beclomethasone, apremilast, sapacitabine, linsitinib, abiraterone, vitamin D analogs (e.g., calcifediol, calcitriol, paricalcitol, doxercalciferol), COX-2 inhibitors (e.g., celecoxib, valdecoxib, rofecoxib), tacrolimus, testosterone, lubiprostone, pharmaceutically acceptable salts thereof, and combinations thereof.

In some embodiments, the lipids in the dosage form may be selected, without limitations, from the group consisting of, almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, *Perilla* oil, pine nut oil, pistachio oil, poppy seed oil, pumpkin seed oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, e.g., in their hydrogenated form, free fatty acids and mono-, di-, and tri-glycerides with C8-, C10-, C12-, C14-, C16-, C18-, C20- and C22-fatty acids, and combinations thereof.

According to certain embodiments, active agents may include lipid-lowering agents including, but not limited to, statins (e.g., lovastatin, simvastatin, pravastatin, fluvastatin, atorvastatin, rosuvastatin, and pitavastatin), fibrates (e.g, clofibrate, ciprofibrate, bezafibrate, fenofibrate, and gemfibrozil), niacin, bile acid sequestrants, ezetimibe, lomitapide, phytosterols, and the pharmaceutically acceptable salts, hydrates, solvates and prodrugs thereof, mixtures of any of the foregoing, and the like.

Suitable nutraceutical active agents may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplement active agents may include vitamins, minerals, fiber, fatty acids, amino acids, herbal supplements or a combination thereof.

Suitable vitamin active agents may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplement active agents may include, but are not limited to, the following: *Arnica*, bilberry, black cohosh, cat's claw, chamomile, *Echinacea*, evening primrose oil, fenugreek, flaxseed, feverfew, garlic, ginger root, *Ginko biloba, Ginseng*, goldenrod, hawthorn, kava-kava, licorice, milk thistle, *Psyllium*, rauowolfia, *Senna*, soybean, St. John's wort, saw palmetto, turmeric, valerian.

Minerals active agents may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Examples of other possible active agents include, but are not limited to, antihistamines (e.g., ranitidine, dimenhydrinate, diphenhydramine, chlorpheniramine and dexchlorpheniramine maleate), non-steroidal anti-inflammatory agents (e.g., aspirin, celecoxib, Cox-2 inhibitors, diclofenac, benoxaprofen, flurbiprofen, fenoprofen, flubufen, indoprofen, piroprofen, carprofen, oxaprozin, pramoprofen, muroprofen, trioxaprofen, suprofen, aminoprofen, fluprofen, bucloxic acid, indomethacin, sulindac, zomepirac, tiopinac, zidometacin, acemetacin, fentiazac, clidanac, oxpinac, meclofenamic acid, flufenamic acid, niflumic acid, tolfenamic acid, diflurisal, flufenisal, piroxicam, sudoxicam, isoxicam, aceclofenac, aloxiprin, azapropazone, benorilate, bromfenac, carprofen, choline magnesium salicylate, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, mefenamic acid, metamizole, methyl salicylate, magnesium salicylate, nabumetone, naproxen, nimesulide, oxyphenbutazone, parecoxib, phenylbutazone, salicyl salicylate, sulindac, sulfinpyrazone, tenoxicam, tiaprofenic acid, tolmetin. pharmaceutically acceptable salts thereof and mixtures thereof) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics tetracycline), (e.g., antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, solvates, and prodrugs thereof.

The active agent that may also be a benzodiazepine, barbiturate, stimulants, or mixtures thereof. The term "benzodiazepines" refers to a benzodiazepine and drugs that are derivatives of a benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, methylphenidate as well as pharmaceutically acceptable salts, hydrates, solvates, prodrugs and mixtures thereof. Benzodiazepine antagonists that can be used as active agent include, but are not limited to, flumazenil as well as pharmaceutically acceptable salts, hydrates, solvates and mixtures thereof.

The term "barbiturates" refers to sedative-hypnotic drugs derived from barbituric acid (2, 4, 6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital as well as pharmaceutically acceptable salts, hydrates, solvates, prodrugs, and mixtures thereof. Barbiturate antagonists that can be used as active agent include, but are not limited to, amphetamines as well as pharmaceutically acceptable salts, hydrates, solvates and mixtures thereof.

The term "stimulants" includes, but is not limited to, amphetamines such as dextroamphetamine resin complex, dextroamphetamine, methamphetamine, methylphenidate, as well as pharmaceutically acceptable salts, hydrates, and solvates and mixtures thereof. Stimulant antagonists that can be used as active agent include, but are not limited to, benzodiazepines, as well as pharmaceutically acceptable salts, hydrates, solvates and mixtures thereof.

The dosage forms according to the disclosure include various active agents and their pharmaceutically acceptable salts thereof. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

As used herein, the terms "therapeutically effective" and an "effective amount" refer to the amount of active agent or the rate at which it is administered which is needed to produce a desired therapeutic result.

As used herein, "shell" or "shell composition" refers to the shell of a softgel capsule which encapsulates a fill material.

As used herein, "conventional enteric polymers" refer to, but are not limited to, acrylic and methacrylic acid polymers, which may be available under the tradename EUDRAGIT® and other conventional acid insoluble polymers, e.g., methyl acrylate-methacrylic acid copolymers. Other conventional acid insoluble polymers include, without limitation, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salts such as sodium alginate and potassium alginate, stearic acid, and shellac. In some embodiments, the enteric shell composition of the present invention does not include an acid insoluble polymer. In other words, the enteric shell composition and the enteric softgel capsule are "free or substantially free of conventional enteric polymers."

All references to wt % throughout the specifications and the claims refer to the weight of the component in reference to the weight of the entire composition and may also be designated as w/w.

As used herein, "fill material" or "fill" refers to the composition that is encapsulated by the enteric capsule shell and contains at least one pharmaceutically active ingredient.

As used herein, "delayed release" refers to releasing the active agent after passing through the stomach.

As used herein, "about" refers to any values that are within a variation of +10%, such that "about 10" would include from 9 to 11. As used herein, "a," "an," or "the" refers to one or more, unless otherwise specified. Thus, for example, reference to "an excipient" includes a single excipient as well as a mixture of two or more different excipients, and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

According to one embodiment, a method for preparing a softgel capsule including treating a softgel capsule with a solution comprising a calcium salt, wherein the softgel capsule includes a fill material and a shell composition. The calcium salt may be calcium chloride, calcium citrate, calcium gluconate, calcium lactate or any other soluble calcium salts.

In some embodiments of the method, the solution may further include hydrochloric acid. In some embodiments, the solution may further include water. In other embodiments, the solution may further include a sugar. The sugar may include dextrose.

In some embodiments of the method, the calcium chloride may be included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the solution.

In certain embodiments of the method, the hydrochloric acid may be included to result in a solution having a pH less than 3.

In some embodiments, the dextrose may be included in the solution in an amount of about 0.1 wt % to about 20 wt %, about 1 wt % to about 19 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the solution.

In some embodiments of the method, the shell composition may include a plasticizer, pectin, gellan gum, dextrose, gelatin, or a combination thereof.

In certain embodiments, the plasticizer may include glycerin, sorbitol, sorbitol sorbitan solution, triacetin, polysorbate, or combinations thereof. In some embodiments, the plasticizer may include glycerin, sorbitol sorbitan solution, or a combination thereof. In yet another embodiment, the plasticizer may be sorbitol sorbitan solution.

In some embodiments, the method may further include drying the softgel capsule. In some embodiments, the drying may be performed by tumbling drying the capsules. In some embodiments, the drying occurs for about 1 hour, about 1.5 hours, about 2 hours, about 3 hours, or about 4 hours. In other embodiments, the method may include drying the capsules in a drying chamber or a drying tunnel.

In some embodiments of the method, the treating may include utilizing a softgel capsule washing/chilling treatment equipment, wherein the softgel capsule is treated with the solution for a pre-determined time period. The softgel capsule washing/chilling treatment equipment may be fully automatic.

In certain embodiments, the pre-determined time period for treating may be about 2.5 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 2 minutes, about 3 minutes, about 4 minutes, about 5 minutes, about 6 minutes, about 7 minutes, about 8 minutes, about 9 minutes, or about 10 minutes.

In other embodiments of the present invention, a softgel capsule is provided. The softgel capsule may include a fill material including an active agent and a shell composition, wherein the shell composition includes calcium ions.

Suitable fill materials comprise at least one pharmaceutically active ingredient and can be made according to known methods. In addition to the at least one pharmaceutically active ingredient, suitable fill materials may comprise additional fill components such as flavoring agents, sweetening agents, coloring agents and fillers or other pharmaceutically acceptable excipients or additives such as synthetic dyes and mineral oxides. Suitable amounts of pharmaceutically active ingredient and pharmaceutically acceptable excipients can be readily determined by one of ordinary skill in the art.

In some embodiments, the shell composition may include pectin. The pectin in the shell composition may be a low methoxy pectin. In an embodiment, the low methoxy pectin may be LM Pectin (P-25), LM Pectin (445C), LM Pectin (100C) or a combination thereof. In another embodiment, the pectin may be amidated pectin or non-amidated pectin. The addition of pectin contributes to the enteric nature of the dosage form. However, too much pectin in the dosage form may reduce the gel strength of the softgel capsule which may in turn adversely affect the sealability of the softgel capsule. Therefore, pectin may be added to the dosage form at a concentration that is sufficiently high to form an enteric dosage form and at the same time is sufficiently low to mitigate the reduction in gel strength. In an embodiment, an amount of pectin in the enteric shell composition is about 1 wt % to about 25 wt %, about 2 wt % to about 20 wt %, from about 3 wt % to about 15 wt %, from about 3 wt % to about 5.5 wt %, from about 5 wt % to about 10 wt %, about 2.5 wt % to about 20 wt %, about 5 wt % to about 18 wt %, 7.5 wt % to about 15 wt %, or about 10 wt % to about 12 wt % based on total weight of the shell composition. The degree of esterification of the pectin incorporated in the shell composition may be lower than about 50%, or may range from about 10% to about 50%, from about 20% to about 40%, or from about 25% to about 35%.

In some embodiments of the capsule, the shell composition may further include a plasticizer. The plasticizer may include glycerin, sorbitol, sorbitol sorbitan solution, triacetin, polysorbate, or combinations thereof. In one embodiment, the plasticizer may include glycerin and sorbitol sorbitan solution. In some embodiments, the polysorbate may include Tween 20, Tween 80 or combinations thereof. Other suitable plasticizers may include, but not be limited to, sugar alcohol plasticizer such as isomalt, maltitol, xylitol, erythritol, adonitol, dulcitol, pentaerythritol, or mannitol; or polyol plasticizer such as diglycerin, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In some embodiments, the amount of plasticizer may be in an amount of about 5 wt % to about 60 wt %, about 10 wt % to about 55 wt %, about 15 wt % to about 50 wt %, about 20 wt % to about 45 wt %, or about 25 wt % to about 35 wt % based on total weight of the shell composition.

In some embodiments of the softgel capsule, the shell composition may further include gelatin. The gelatin may include Type A gelatin, Type B gelatin, a hide gelatin and/or a bone gelatin used alone or in combination. In one embodiment, the gelatin is a 250 bloom gelatin. In another embodiment, there is only one type of gelatin. In yet another embodiment, the gelatin is a combination of at least two types of gelatins. In an embodiment, the amount of gelatin in the enteric shell composition is about 10 wt % to about 80 wt %, about 15 wt % to about 60 wt %, about 20 wt % to about 55 wt %, about 25 wt % to about 50 wt %, about 30 wt % to about 45 wt %, or about 35 wt % to about 40 wt % based on total weight of the shell composition.

In some embodiments, the shell composition of the softgel capsule may also include gellan gum, dextrose, water or a combination thereof. In some embodiments, the amount of dextrose may be about 0.001 wt % to about 5 wt %, about 0.01 wt % to about 4.5 wt %, about 0.01 wt % to about 4 wt %, about 0.1 wt % to about 3 wt %, or about 1 wt % to about 2.5 wt % based on total weight of the shell composition.

In some embodiments, the amount of gellan gum may be included in an amount of about 0.001 wt % to about 5 wt %, about 0.01 wt % to about 4 wt %, about 0.1 wt % to about 3 wt %, or about 1 wt % to about 2 wt %, based on total weight of the shell composition.

In some embodiments, the softgel capsule may be treated with a treatment solution. The treatment solution may include a calcium salt. The calcium salt may be calcium chloride, calcium citrate, calcium gluconate, calcium lactate or any other soluble calcium salts. In an embodiment, the calcium salt may be calcium chloride.

In some embodiments, the calcium salt may be included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the treatment solution.

In some embodiments, the treatment solution may further include water. In other embodiments, the treatment solution may further include a sugar. The sugar may be dextrose. The sugar or dextrose may be included in an amount of about 0.1 wt % to about 20 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the treatment solution.

In some embodiments, the softgel capsule may be treated with the calcium treatment solution. The treatment may provide a weight gain of about 1% to about 10%, about 2% to about 8%, or about 3% to about 5% of the capsule.

In some embodiments, after treatment the capsule may have an improved burst strength when compared to a capsule without the treatment of the present invention.

In an embodiment, the shell composition of the softgel capsule may optionally comprise additional agents such as coloring agents, flavorings agents, sweetening agents, fillers, antioxidants, diluents, pH modifiers or other pharmaceutically acceptable excipients or additives such as synthetic dyes and mineral oxides.

Exemplary suitable coloring agents may include, but not be limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but not be limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but not be limited to, breath freshening compounds like menthol, spearmint, and cinnamon, coffee beans, other flavors or fragrances such as fruit flavors (e.g., cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but not be limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), *Stevia*, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In some embodiments, the softgel capsule does not rupture at a rupture at a pH of 1.2 at 15 minutes, 30 minutes, 45 minutes, 60 minutes, 75 minutes, 90 minutes, 105 minutes, or 120 minutes when measured with a USP Apparatus II with paddles at 50 RPM, or 100 RPM in 0.1N hydrochloric acid (HCl) acidic media.

In some embodiments, the softgel capsule does not rupture at a pH of 3.0, pH of 4.0, or pH of 5.0 at 15 minutes, 30 minutes, 45 minutes, 60 minutes, 75 minutes or 90 minutes when measured with a USP Apparatus II with paddles at 50 RPM, or 100 RPM in acidic media.

In some embodiments, the capsule ruptures at a pH of between 6 and 8 at 5 minutes, 10 minutes, 15 minutes, 20 minutes, 25 minutes, 30 minutes, 35 minutes, 40 minutes, 45 minutes, 50 minutes, 55 minutes, or 60 minutes when measured with a USP Apparatus II with paddles at 50 RPM, 100 RPM, 150 RPM, or 200 RPM in phosphate buffer.

Encapsulation of the fill material can be accomplished in any conventional manner. As an example, a rotary die encapsulation may be used.

According to an embodiment, an enteric softgel capsule is prepared by the process comprising the steps of: preparing the fill material, the fill material including an active agent; encapsulating the fill material in a shell composition forming a softgel capsule. The capsule is then treated with a treatment solution including a calcium source, such as calcium chloride, calcium chloride dihydrate ($CaCl_2 \cdot 2H_2O$), calcium citrate, calcium gluconate or calcium lactate. The treating includes utilizing a fully automatic softgel capsule washing/chilling treatment equipment. The softgel capsule is further dried after treatment using a tumble dryer, in a drying chamber or a drying tunnel.

LIST OF ITEMS

1. A method for preparing a softgel capsule comprising: treating a softgel capsule with a solution comprising a calcium salt, wherein the softgel capsule comprises a fill material and a shell composition.
2. The method of item 1, wherein the calcium salt comprises calcium chloride, calcium citrate, calcium gluconate, calcium lactate or a combination thereof.
3. The method of item 1, wherein the solution further comprises hydrochloric acid.
4. The method of item 1, wherein the solution further comprises water.
5. The method of any one of items 1-4, wherein the solution further comprises a sugar.
6. The method of item 5, wherein the sugar comprises dextrose.
7. The method of any of the preceding items, wherein the calcium salt is included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the solution.
8. The method of item 3, wherein the pH of the solution is less than 3.
9. The method of item 6, wherein the dextrose is included in an amount of about 0.1 wt % to about 20 wt %, about 1 wt % to about 19 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the solution.
10. The method of any of the preceding items, wherein the shell composition comprises a plasticizer, pectin, gellan gum, dextrose, gelatin, or a combination thereof.
11. The method of item 10, wherein the plasticizer comprises glycerin, sorbitol, sorbitol sorbitan solution, triacetin, polysorbate, or combinations thereof.
12. The method of item 10, wherein the plasticizer comprises glycerin, sorbitol sorbitan solution, or a combination thereof.
13. The method of item 10, wherein the plasticizer is sorbitol sorbitan solution.
14. The method of any of the preceding items, further comprising drying the capsules after treating the capsules.
15. The method of item 14, wherein the drying is performed by tumble drying the capsules.
16. The method of item 14, wherein the drying occurs for about 5 minutes to about 6 hours, 15 minutes to about 5 hours, 30 minutes to about 4 hours, 45 minutes to about 3 hours, about 1 hour to about 2.5 hours or about 1.5 hours to about 2 hours.
17. The method of item 14, wherein the drying is performed in a drying chamber or a drying tunnel.
18. The method of any of the preceding items, wherein the treating includes using a washing/chilling treatment equipment for a pre-determined time period.

19. The method of item 18, wherein the washing/chilling treatment equipment is fully or partially automatic.
20. The method of item 18, wherein the washing/chilling treatment equipment is jacketed, and can be cooled or chilled using an external chiller.
21. The method of item 18, wherein the time period is about 2.5 seconds, about 5 seconds to about 10 minutes, about 10 seconds to about 9 minutes, about 15 seconds to about 8 minutes, about 20 seconds to about 7 minutes, about 25 seconds to about 6 minutes, about 30 seconds to about 5 minutes, about 35 seconds to about 4 minutes, about 40 seconds to about 3 minutes, about 45 seconds to about 2 minutes, or about 50 seconds to about 1 minute.
22. A softgel capsule comprising:
    a fill material comprising an active agent; and
    a shell composition, wherein the shell composition includes calcium ions.
23. The softgel capsule of item 22, wherein the shell composition comprises pectin.
24. The softgel capsule of item 23, wherein the pectin is low methoxy pectin.
25. The softgel capsule of item 23, wherein the pectin is included in an amount of about 1 wt % to about 25 wt %, about 2 wt % to about 20 wt %, 5 wt % to about 18 wt %, 7.5 wt % to about 15 wt %, or about 10 wt % to about 12 wt %, based on total weight of the shell composition.
26. The softgel capsule of item 22, wherein the shell composition comprises a plasticizer.
27. The softgel capsule of item 26, wherein the plasticizer comprises glycerin, sorbitol, sorbitol sorbitan solution, triacetin, polysorbate, or combinations thereof.
28. The softgel capsule of item 26, wherein the plasticizer comprises glycerin and sorbitol sorbitan solution.
29. The softgel capsule of item 27, wherein the polysorbate comprises Tween 20, Tween 80, or combinations thereof.
30. The softgel capsule of item 26, wherein the plasticizer is included in an amount of about 5 wt % to about 60 wt %, about 10 wt % to about 55 wt %, about 15 wt % to about 50 wt %, about 20 wt % to about 45 wt %, or about 25 wt % to about 35 wt % based on total weight of the shell composition.
31. The softgel capsule of item 22, wherein the shell composition comprises gelatin.
32. The softgel capsule of item 31, wherein the gelatin is selected from the group consisting of Type A gelatin, Type B gelatin, and mixtures thereof.
33. The softgel capsule of item 31, wherein the gelatin is selected from the group consisting of fish gelatin, hide gelatin, bone gelatin and mixtures thereof.
34. The softgel capsule of item 31, wherein the gelatin is included in an amount of about 15 wt % to about 60 wt %, about 20 wt % to about 55 wt %, about 25 wt % to about 50 wt %, about 30 wt % to about 45 wt %, or about 35 wt % to about 40 wt % based on total weight of the shell composition.
35. The softgel capsule of item 22, wherein the shell composition comprises gellan gum.
36. The softgel capsule of item 35, wherein the gellan gum is included in an amount of about 0.001 wt % to about 5 wt %, about 0.01 wt % to about 4 wt %, about 0.1 wt % to about 3 wt %, or about 1 wt % to about 2 wt % based on total weight of the shell composition.
37. The softgel capsule of item 22, wherein the shell composition comprises dextrose.
38. The softgel capsule of item 37, wherein the dextrose is included in an amount of about 0.001 wt % to about 5 wt %, about 0.01 wt % to about 4.5 wt %, about 0.05 wt % to about 4 wt %, about 0.1 wt % to about 3 wt %, or about 1 wt % to about 2.5 wt % based on total weight of the shell composition.
39. The softgel capsule of item 22, wherein the softgel capsule is treated with a treatment solution comprising calcium chloride.
40. The softgel capsule of item 39, wherein the calcium chloride is included in an amount of about 1 wt % to about 25 wt %, about 2 wt % to about 22 wt %, about 3 wt % to about 20 wt %, about 4 wt % to about 18 wt %, about 5 wt % to about 16 wt %, about 6 wt % to about 14 wt %, or about 7 wt % to about 12 wt %, based on total weight of the treatment solution.
41. The softgel capsule of item 39, wherein the treatment solution further comprises water.
42. The softgel capsule of item 39 or 41, wherein the treatment solution further comprises a sugar.
43. The softgel capsule of item 42, wherein the sugar comprises dextrose.
44. The softgel capsule of item 43, wherein the dextrose is included in an amount of about 0.1 wt % to about 20 wt %, about 2 wt % to about 18 wt %, about 3 wt % to about 16 wt %, about 4 wt % to about 14 wt %, about 5 wt % to about 12 wt %, or about 6 wt % to about 10 wt %, based on total weight of the treatment solution.
45. The softgel capsule of any one of items 39, 41, or 42, wherein the treatment solution further comprises hydrochloric acid.
46. The softgel capsule of any one of items 39-45, wherein the treatment provides a weight gain of about 1% to about 10% of the capsule.
47. The softgel capsule of any one of items 22-46, wherein the capsule has an improved burst strength when compared to a capsule without calcium.
48. The softgel capsule of any one of items 22-47, wherein the capsule does not rupture at a pH of 1.2 at 15 minutes, 30 minutes, 45 minutes, 60 minutes, 75 minutes, 90 minutes, 105 minutes, or 120 minutes when measured with a USP Apparatus II with paddles at 50 RPM, or 100 RPM in 0.1N hydrochloric (HCl) acid acidic media.
49. The softgel capsule of any one of items 22-47, wherein the capsule does not rupture at a pH of 3.0, pH of 4.0, pH of 5.0 at 15 minutes, 30 minutes, 45 minutes, 60 minutes, 75 minutes, or 90 minutes when measured with a USP Apparatus II with paddles at 50 RPM, or 100 RPM in acidic media with above pH.
50. The softgel capsule of any one of items 22-47, wherein the capsule ruptures at a pH of between 6 and 8 at less than 5 minutes, less than 10 minutes, less than 15 minutes, less than 20 minutes, less than 25 minutes, less than 30 minutes, less than 35 minutes, less than 40 minutes, less than 45 minutes, less than 50 minutes, less than 55 minutes, or less than 60 minutes when measured with a USP Apparatus II with paddles at 50 RPM, 100 RPM, 150 RPM, or 200 RPM in phosphate buffer.

EXAMPLES

Specific embodiments of the invention will now be demonstrated by reference to the following examples. It should be understood that these examples are disclosed solely by way of illustrating the invention and should not be taken in any way to limit the scope of the present invention.

Experimental Procedures and Methods

Calcium Chloride Solution

Among all available types of calcium ion resource for initiating the calcium bridging effect, calcium chloride was considered as the preferable choice because of its low cost and higher solubility. To simplify the procedure, weight percentage was used for all different concentrations of calcium chloride solution. The examples of 5% and 10% calcium chloride basic formulas are listed in Table 1.

Pectin ionotropic gelation is pH dependent. The gel network is more stable at lower pH (less than 5) than in higher pH (higher than 7) environment. The pH values of calcium chloride solutions were adjusted intentionally from pH >8 to pH<3 with 0.1 N hydrochloride solution which is an important finding of this study.

TABLE 1

Calcium Chloride Aqueous Solutions

| Ingredients | CAS Number | 5% Solution w/w % | 10% Solution w/w % |
|---|---|---|---|
| Calcium Chloride, anhydrous ($CaCl_2$) | 10043-52-4 | 5.00 | 10.00 |
| Purified Water (Aqua) | 7732-18-5 | 95.00 | 90.00 |
| Total | | 100.00 | 100.00 |

Calcium Chloride and Hydrochloric Acid Solution

| Calcium Chloride, anhydrous ($CaCl_2$) | 10043-52-4 | 5.00 | 10.00 |
|---|---|---|---|
| Purified Water (Aqua) | 7732-18-5 | 95.00 | 90.00 |
| Hydrochloric Acid | 7647-01-0 | To achieve pH < 3 | To achieve pH < 3 |
| Total | | 100.00 | 100.00 |

Calcium Chloride and Dextrose Solution

Reducing sugars, such as dextrose contain free aldehyde or ketone group and may be classified as typical crosslinkers to induce covalent cross-linking. By adding dextrose as a reducing sugar to the calcium chloride solution, it may enhance the enteric function on the surface of softgel capsules. The examples of 10% calcium chloride and 5% or 10% dextrose solution basic formulas are listed in Table 2. The pH values of calcium chloride/dextrose solutions were also adjusted intentionally to pH<3 with 0.1N hydrochloride solution.

TABLE 2

Calcium Chloride and Dextrose Aqueous Solutions

| Ingredients | CAS Number | 10% + 5% Solution w/w % | 10% + 10% Solution w/w % |
|---|---|---|---|
| Calcium Chloride, anhydrous ($CaCl_2$) | 10043-52-4 | 10.00 | 10.00 |
| Purified Water (Aqua) | 7732-18-5 | 85.00 | 80.00 |
| Dextrose Anhydrous | 50-99-7 | 5.00 | 10.00 |
| Total | | 100.00 | 100.00 |

Softgel Capsules

Softgel capsules from different manufactured batches (Samples 1-5) were utilized to evaluate the calcium treatment. The gel mass formulations used to manufacture these three lots are shown in Table 3.

TABLE 3

Qualitative Shell Formulations

| Ingredient | Sample 1 (%) | Sample 2 (%) | Sample 3 (%) | Sample 4 (%) | Sample 5 (%) |
|---|---|---|---|---|---|
| Sorbitol sorbitan solution | 4-22 | 4-22 | 6-25 | 6-25 | 6-25 |
| Glycerin | 4-18 | 4-18 | 6-18 | 2-15 | — |
| Pectin | 3-12 | 3-12 | 6-14 | 3-12 | 3-12 |
| Gellan gum | — | — | 0.2-2 | 0.01-1 | — |
| Dextrose Anhydrous | 0.01-0.4 | 0.01-0.4 | 0.02-2.0 | 0.01-0.4 | 0.01-0.4 |
| Gelatin | 28-52 | 28-52 | 25-48 | 28-48 | 28-52 |

After the capsules were tumble dried in the regular encapsulation process, capsules were collected and treated by dipping capsules into a stainless-steel container with filtering basket that contained 3 liters of calcium chloride solution for different periods of time (5 seconds, 10 seconds, and 20 seconds, respectively). About 500 capsules were manually treated at each time point. After calcium treatment, capsules were tumble dried in a tumble drier for 1 hour to remove the excess water on the shell that was introduced by the calcium treatment. Treated capsules were then dried in drying chamber later as per the standard softgel tunnel drying process.

Some of the finished capsules were also treated with calcium chloride and dextrose solution or calcium chloride solution for a longer treatment time to evaluate the upper limit of treatment time and the effectiveness of dextrose addition.

For fully integrated into the current encapsulation process, the calcium treatment or the calcium and dextrose treatment step can be added into the process chain right before tumble drying in a regular softgel manufacturing process with fully automated equipment.

The fully automated equipment consist of a jacketed rectangular container or calcium treatment solution reservoir with a build-in conveyor. The treatment time can be regulated by adjusting the speed of the conveyor belt. The temperature of the calcium solution can be maintained by an external chiller hooking up to the jacketed container.

Summary of Testing Results

Weight Gain of Calcium Treatment

After calcium treatment, treated capsules were expected to gain a small amount of weight. Table 4 summarized the weight gain data from the untreated and treated fresh capsules and dried finished capsules.

TABLE 4

Summary of Weight Gain (Sample 1)

| Calcium Treatment | Drying Condition | Capsule Weight (g) | Shell Weight (g) | Weight Gain (g) | Weight Gain (%) |
|---|---|---|---|---|---|
| Untreated | Before Tumble Drying | 1.232 | 0.532 | — | — |
| | Dried Product | 1.050 | 0.35 | — | — |
| 5% $CaCl_2$, 5 sec treated | Freshly treated | 1.266 | 0.566 | 0.034 | 6.39% |
| | Dried Product | 1.063 | 0.363 | 0.013 | 3.71% |
| 5% $CaCl_2$, | Freshly treated | 1.291 | 0.591 | 0.059 | 11.09% |

TABLE 4-continued

Summary of Weight Gain (Sample 1)

| Calcium Treatment | Drying Condition | Capsule Weight (g) | Shell Weight (g) | Weight Gain (g) | Weight Gain (%) |
|---|---|---|---|---|---|
| 20 sec treated | Dried Product | 1.064 | 0.364 | 0.014 | 4.00% |
| 10% CaCl$_2$, 5 sec treated | Freshly treated | 1.280 | 0.58 | 0.048 | 9.02% |
| | Dried Product | 1.066 | 0.366 | 0.016 | 4.57% |
| 10% CaCl$_2$, 20 sec treated | Freshly treated | 1.290 | 0.59 | 0.058 | 10.90% |
| | Dried Product | 1.060 | 0.365 | 0.015 | 4.29% |

Compared to the untreated wet capsules, the weight gains right after calcium treatment vary from 35 mg to 59 mg per capsules or 6.4% to 11.1% of the shell weight depending on the contact time. The weight gains of dried calcium treated product were between 13-16 mg per capsule or 3.7-4.6% of the shell weight.

Weight Gain of Calcium and Dextrose Treatment

Table 5 summarizes the weight gain data from the untreated and treated finished dried capsules with 1 minute, 2 minutes and 5 minutes contact times.

TABLE 5

Summary of Weight Gain (Sample 2, 20 Oblong)

| Treatment Condition | Treatment Time | Capsule Weight (g) | Shell Weight (g) | Weight Gain (g) | Weight Gain (%) |
|---|---|---|---|---|---|
| 10% CaCl$_2$ + 5% Dextrose | 1 minute | 1.514 | 0.514 | 0.060 | 11.67% |
| | 2 minutes | 1.513 | 0.513 | 0.079 | 15.40% |
| | 5 minutes | 1.510 | 0.510 | 0.115 | 22.55% |
| 10% CaCl$_2$ + 10% Dextrose | 1 minute | 1.510 | 0.510 | 0.055 | 10.78% |
| | 2 minutes | 1.509 | 0.509 | 0.075 | 14.73% |
| | 5 minutes | 1.510 | 0.510 | 0.109 | 21.37% |

Compared to the untreated dried finished capsules, the weight gains of calcium and dextrose treated product were between 55-115 mg per capsule or 10.8-22.6% of the shell weight. The concentration of solution does not affect capsule weight gain, treatment time is the only factor.

Low methyl amidated (LMA) pectin is sensitive to the presence of calcium ions and more tolerant of calcium content compared to high methyl (HM) pectin and low methyl (LM) pectin. LMA will gel over a wider range of calcium concentrations, however, the pectin gel strength will reach its maximum level at around 40 mg Ca$^{2+}$ per gram of pectin, then the gel strength will be lower with increase of calcium ion concentration. The weight gain should be carefully controlled by limiting the treatment time.

Capsules Moisture Absorption Test

Capsule moisture absorption tests were conducted by exposing capsules to 0.1N HCl solution for certain times and recording the capsules weight gain. Table 6 summarizes the moisture absorption data for the untreated and treated finished dried capsules with 1 minute, 2 minutes and 5 minutes contact times, respectively. FIG. 1 shows the capsule moisture absorption comparison between tested capsules.

TABLE 6

Capsules Moisture Absorption Results of Selected Softgel Capsules (Per Capsule)

| Treatment Condition | Treatment Time | Weight Gain 5 minutes | Weight Gain 10 minutes |
|---|---|---|---|
| 10% CaCl$_2$ + 5% Dextrose | 1 minute | 12.7% | 18.5% |
| | 2 minutes | 12.4% | 19.0% |
| | 5 minutes | 12.9% | 18.4% |
| 10% CaCl$_2$ + 10% Dextrose | 1 minute | 12.5% | 18.9% |
| | 2 minutes | 12.9% | 17.8% |
| | 5 minutes | 13.4% | 18.4% |
| Untreated | N/A | 15.4% | 22.6% |

Untreated softgel capsules had more than 15.4% weight gain after 5 minutes and 22.6% weight gain after 10 minutes, which indicates stronger moisture absorption. Both calcium plus dextrose treated softgel capsules have very similar weight gain after 5 minutes and 10 minutes exposure to the acid medium, and less weight gain when compared to untreated capsules. This indicated better moisture barrier that provided by the calcium and dextrose treatment.

Capsule Appearance

The fresh softgel capsules treated with 5% calcium chloride aqueous solution were clear and transparent with slightly improved shape. No obvious difference was identified when compared to untreated capsules. Softgel capsules treated with 10% calcium chloride aqueous solution for 20 seconds showed a slightly hazy appearance. Therefore, treatment time is preferred to be within about 10 seconds if 10% calcium chloride solution is used. The dried finished softgel capsules treated with calcium chloride and dextrose solution were clear and transparent. No obvious difference was identified when compared to untreated capsules.

Capsules Burst Strength

Burst strength of softgel capsules is an indicator of capsule seal quality. This is a key quality attribute for softgel capsules and indicates how strong the softgel seals or how brittle the capsule is. The burst strength data of all 47 samples was collected by using Texture Analyzer TA. HD Plus and is summarized in Table 7.

From the results, the burst strength of calcium treated capsules for lot Sample 3 was significantly higher than that of untreated capsules. The burst strength of capsules treated with 10% CaCl$_2$) for both 5 and 20 seconds were significantly higher than the burst strength of capsules treated with 5% CaCl$_2$) for both 5 and 20 seconds for lot Sample 1. Thus, it was believed that the calcium treatment introduced the calcium bridging effect, which creates a stronger complex gelation. Therefore, the robustness of softgel capsules was improved.

TABLE 7

Burst Strength of Dried Softgel Capsules

| Sample | Burst Strength (kg) | Travel Dis. (mm) |
|---|---|---|
| Sample 3, Untreated | 89.3 | 5.49 |
| Sample 3 (5% CaCl$_2$, 5 sec treated) | 126.6 | 6.14 |
| Sample 3 (5% CaCl$_2$, 20 sec treated) | 130.1 | 6.25 |

TABLE 7-continued

Burst Strength of Dried Softgel Capsules

| Sample | Burst Strength (kg) | Travel Dis. (mm) |
|---|---|---|
| Sample 1, Untreated | 53.6 | 4.13 |
| Sample 1 (5% CaCl$_2$, 5 sec treated) | 64.0 | 4.59 |
| Sample 1 (5% CaCl$_2$, 20 sec treated) | 55.4 | 4.27 |
| Sample 1 (10% CaCl$_2$, 5 sec treated) | 101.1 | 5.37 |
| Sample 1 (10% CaCl$_2$, 20 sec treated) | 108.8 | 5.48 |

Capsule Disintegration Test

The disintegration test is considered as standard enteric function test in both USP and EP. It is critical that the finished product pass the required disintegration test described in the finished product specification. To evaluate the quality of untreated finished softgel capsules and calcium treated capsules, the two stage disintegration tests were performed on both treated and untreated capsules per EP and USP standards. In this study, maximum 2 hours acidic stage disintegration tests were performed, and the extended buffer stage disintegration tests were only performed on selected calcium treated softgels and untreated softgels.

Table 8 summarizes the test results of fresh calcium chloride treated finished capsules from different batches.

TABLE 8

Summary of 2-hour Disintegration Test of Selected Finished Capsules (USP APP B in 0.1N HCl (pH = 1.2 ± 0.2) for 2 hours max)

| Sample | Calcium Treatment | Average Disintegration Time | Note |
|---|---|---|---|
| Sample 3 | No | 55 minutes | Avg. 6 capsules |
| Sample 3 | 5% CaCl$_2$, 5 sec | 106 minutes | 4 of 6 capsules did not rupture |
| Sample 3 | 5% CaCl$_2$, 20 sec | Intact* | 5 of 6 capsules did not rupture, 1 ruptured at 69 minutes |
| Sample 1 | No | 69 minutes | Avg. 6 capsules |
| Sample 1 | 5% CaCl$_2$, 5 sec | Intact | Avg. 6 capsules |
| Sample 2 | No | 45 minutes | Avg. 6 capsules |
| Sample 2 | 5% CaCl$_2$, 5 sec | 79 minutes | Avg. 6 capsules |
| Sample 2 | 5% CaCl$_2$, 10 sec | Intact | Avg. 6 capsules |
| Sample 2 | 5% CaCl$_2$, 20 sec | Intact | Avg. 6 capsules |

*Wrong alignment of capsule caused early rupture of the 1 capsule

The disintegration time of calcium treated capsules in acidic medium was significantly longer than the untreated capsules. The preliminary results demonstrate that the calcium bridging effect enhanced the enteric function of softgel capsules. The capsules treated for 20 seconds with 5% calcium chloride solution showed better enteric performance in acidic medium than the one treated with the shorter time.

Finished dried softgel capsules from lot Sample 2 were selected to be treated with two different concentrations of calcium chloride and dextrose solution for 1 minute, 2 minutes and 5 minutes, respectively. Table 9 summarizes the test results of calcium and dextrose solution treated dried finished capsules. Again, only maximum 2 hours acidic stage disintegration tests were performed. Also, capsules from the same batch were treated for 15 minutes with 5% calcium chloride solution to challenge the contact time limitation.

TABLE 9

Summary of 2-hour Disintegration Test of Sample 2 Finished Capsules (USP APP B in 0.1N HCl (pH = 1.2 ± 0.2) for 2 hours max)

| Treatment Solution | Treatment time | Average Disintegration Time | Note |
|---|---|---|---|
| 10% CaCl$_2$, + 5% Dextrose | 1 minute | 82 minutes | 2 of 3 capsules did not rupture |
|  | 2 minutes | 75 minutes | 2 of 3 capsules did not rupture |
|  | 5 minutes | 64 minutes | Avg. 3 capsules |
| 10% CaCl$_2$, + 10% Dextrose | 1 minute | 76 minutes | 1 of 3 capsules did not rupture |
|  | 2 minutes | 72 minutes | 2 of 3 capsules did not rupture |
|  | 5 minutes | 61 minutes | 2 of 3 capsules did not rupture |
| 10% CaCl$_2$ | 15 minutes | 61 minutes | Avg. 6 capsules |

Capsules treated for 5 minutes did not perform as good as treated for 1 minutes and 2 minutes, which confirmed that excessive load of calcium ions reduced the gel enteric function. Adding dextrose to the calcium treatment has not showed the significant benefit for the improvement of enteric properties yet.

Table 10 summarizes the two stage disintegration test results of calcium chloride treated and untreated finished capsules from Samples 4 and 5.

TABLE 10

Summary of Two-Stage Disintegration Test of Selected Finished Capsules (USP APP B in 0.1N HCl (pH = 1.2 ± 0.2) for 2 hours max and in phosphate buffer (pH = 6.8 ± 0.2) for extended test time)

| Sample | Sampling Point | Calcium Treatment | | Average Disintegration Time |
|---|---|---|---|---|
| Sample 4 | T0 | None | Acid | 98 minutes |
|  |  |  | Buffer | 13 minutes |
|  |  | 10% CaCl$_2$, 10 sec | Acid | Intact |
|  |  |  | Buffer | 48 minutes |
|  | T = 3 M (Ambient) | None | Acid | 102 minutes |
|  |  |  | Buffer | 13 minutes |
|  |  | 10% CaCl$_2$, 10 sec | Acid | Intact |
|  |  |  | Buffer | 48 minutes |
| Sample 5 | T0 | None | Acid | 91 minutes |
|  |  |  | Buffer | 11 minutes |
|  |  | 10% CaCl$_2$, 10 sec | Acid | Intact |
|  |  |  | Buffer | 48 minutes |
|  | T = 3 M (Ambient) | None | Acid | 84 minutes |
|  |  |  | Buffer | 10 minutes |
|  |  | 10% CaCl$_2$, 10 sec | Acid | Intact |
|  |  |  | Buffer | 63 minutes |

The disintegration time of calcium treated capsules in acidic medium stayed intact for two hours, and in buffer medium were significantly longer than the untreated capsules. The results demonstrate that the calcium bridging effect enhanced the enteric function of softgel capsules. The enhancement of enteric function induced by calcium treatment is stable and consistent.

Capsules Two-Stage Dissolution Test

The two-stage dissolution test is also considered as standard enteric function test in both USP and EP methods. It is critical that the enteric products pass the required two-stage dissolution test described in product specification as well. To evaluate the quality of finished softgel capsules and calcium treated capsules, two stage dissolution tests were performed on both treated and un-treated capsules in selected batches.

From previous development work, we found that a curing process is necessary for pectin-gelatin polyelectrolyte complexes system to complete and to be able to provide the required enteric functionality. To complete the formation of the interaction complex, the curing time may require a minimum one to four weeks at ambient conditions. If the finished capsules were tested before the completion of curing, a premature release may be observed in the first 5-15 minutes of two stage dissolution tests. To shorten or eliminate the curing time and to make the softgel capsule more efficient, the calcium treatment can reduce or even eliminate the curing time. Table 11 summarizes the data on test results of capsules from different batches.

TABLE 11

Summary of Two Stage Dissolution Test of Sample 1 (USP APP II-in 0.1N HCl (pH = 1.2 ± 0.2) for 2 hours followed by testing in converted Phosphate buffer pH 6.8 ± 0.2)

| Sample | Calcium Treatment | Stage | Average Rupture Time |
|---|---|---|---|
| Sample 1 | None (1 week from DOM*) | Acid | 2 out of 6 showed premature release at 4 mins |
|  |  | Buffer | Ruptured in 4 minutes |
|  | 5% CaCl$_2$, 5 sec treated (1 week from DOM) | Acid | Intact |
|  |  | Buffer | Ruptured in 7 minutes |
|  | 5% CaCl$_2$, 20 sec treated (1 week from DOM) | Acid | Intact |
|  |  | Buffer | Ruptured in 9 minutes |
|  | 10% CaCl$_2$, 5 sec treated (1 week from DOM) | Acid | Intact |
|  |  | Buffer | Ruptured in 8 minutes |

*Date of Manufacturing

The test data clearly showed that even within one week after manufacturing, all calcium treated capsules passed two-stage rupture tests without any premature release observed, while 2 out of 6 the untreated capsules from same batch still had premature release. Also, all treated capsules ruptured in buffer stage within 10 minutes, which confirmed that the calcium ion-initiated pectin ionotropic gelation is pH dependent.

High pH Tolerance

The pH value of human stomach fluid may vary time by time. The normal volume of the stomach fluid is 20 to 100 mL and the pH is acidic (1.5 to 3.5). However, pH of stomach fluid may increase during food digestion. To guarantee to deliver the enteric function in all pH value range, it is important that capsules can tolerant a higher pH environment for certain periods of time. From previous studies of capsules made with pectin and gelatin gel, capsules could only stay intact for approximately 30 minutes in pH 5 media before rupture. Table 12 summarizes the data on the test results of capsules from different batches after calcium treatment in pH 5 medium.

TABLE 12

Summary of Higher PH Tolerance Test

| Sample | Calcium Treatment | pH value | Rupture Time | Test Time Point |
|---|---|---|---|---|
| Sample 1 | None | 5.0 | 26 minutes | 9 weeks from DOM |
|  | 5% CaCl$_2$, 5 sec treated | 5.0 | 70 minutes | 1 week from DOM |
|  | 5% CaCl$_2$, 5 sec treated | 5.0 | 71 minutes | 4 weeks from DOM |
|  | 10% CaCl$_2$, 20 sec treated | 5.0 | 110 minutes | 1 week from DOM |
| Sample 3 | None | 5.0 | 35 minutes | 6 weeks from DOM |
|  | 5% CaCl$_2$, 5 sec treated | 5.0 | 56 minutes | 1 week from DOM |
|  | 5% CaCl$_2$, 20 sec treated | 5.0 | 83 minutes | 1 week from DOM |

The rupture time of calcium treated capsules in pH 5 media is significantly longer than untreated capsules. This indicated that calcium treatment enhanced the high pH tolerance of softgel capsules. The longer calcium treatment time, the higher pH tolerance the capsules had.

SUMMARY AND CONCLUSIONS

The data summarized in this study demonstrated the benefit of calcium treatment of softgels. Calcium treatment has provided multiple benefits to the softgel capsules including but not limited to:
1. Minimum change to current gel formulation or process by incorporating an inline calcium treatment step after encapsulation.
2. The same appearance and slightly improved shape.
3. No curing time required prior to conducting the two-stage rupture or disintegration tests.
4. Improved moisture barrier in acid medium.
5. Improved enteric performance: pass two-stage rupture test and two-stage disintegration test (Both USP and EP)
6. Improved high pH tolerance. Stay intact for one hour pH 5.0 media.
7. Addition of dextrose to calcium has not shown any advantage in the short-term storage. However, as the dextrose cross-linking takes time, on-going long-term stability studies are expected to demonstrate further enhanced enteric functionality.

Calcium treatment or calcium and dextrose treatment has the optimum treatment time which allow the pectin gelation to reach its maximum gel strength and enteric functionality. Calcium and dextrose treatment doesn't show significant difference compared to calcium only treatment in the short term. The effectiveness of adding dextrose will be further evaluated.

Also, due to enhanced enteric function and performance, the target ribbon thickness of capsule may potentially be reduced with calcium treatment, resulting in lower raw material cost.

The preceding description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail in order to avoid unnecessarily obscuring the present invention. Thus, the specific details set forth are exemplary. Particular embodiments may vary from these exemplary details and still be contemplated to be within the scope of the present invention.

Although the operations of the methods herein are described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for treating a softgel capsule comprising applying a treatment solution to a softgel capsule, wherein the treatment solution comprises a calcium salt and a sugar, wherein the softgel capsule comprises a fill material and a shell composition.

2. The method of claim 1, wherein the calcium salt comprises calcium chloride, calcium citrate, calcium gluconate, calcium lactate or a combination thereof.

3. The method of claim 1, wherein the solution further comprises hydrochloric acid.

4. The method of claim 1, wherein the solution further comprises water.

5. The method of claim 1, wherein the sugar comprises dextrose.

6. The method of claim 1, wherein the calcium salt is included in an amount of about 1 wt % to about 25 wt %, based on the total weight of the solution.

7. The method of claim 3, wherein the pH of the solution is less than 3.

8. The method of claim 5, wherein the dextrose is included in an amount of about 0.1 wt % to about 20 wt %, based on the total weight of the solution.

9. The method of claim 1, wherein the shell composition comprises a plasticizer, pectin, gellan gum, dextrose, gelatin, or a combination thereof.

10. The method of claim 9, wherein the plasticizer comprises glycerin, sorbitol, sorbitol sorbitan solution, triacetin, polysorbate, or combinations thereof.

11. The method of claim 9, wherein the plasticizer comprises glycerin, sorbitol sorbitan solution, or a combination thereof.

12. The method of claim 9, wherein the plasticizer is sorbitol sorbitan solution.

13. The method of claim 1, further comprising drying the capsules after treating the capsules.

14. The method of claim 13, wherein the drying is performed by tumble drying the capsules.

15. The method of claim 13, wherein the drying occurs for about 5 minutes to about 6 hours.

16. The method of claim 13, wherein the drying is performed in a drying chamber or a drying tunnel.

17. The method of claim 1, further comprising adding the softgel capsule to washing treatment equipment, and applying the treatment solution for a time period of about 5 seconds to about 10 minutes.

18. The method of claim 17, wherein the washing treatment equipment is fully automatic.

19. The method of claim 17, wherein the washing treatment equipment is jacketed, and the washing equipment is cooled or chilled using an external chiller.

* * * * *